US005329705A

United States Patent [19]
Grim et al.

[11] Patent Number: 5,329,705
[45] Date of Patent: Jul. 19, 1994

[54] FOOTGEAR WITH PRESSURE RELIEF ZONES

[75] Inventors: Tracy E. Grim, Broken Arrow; Kevin R. O'Donnell, Thousand Oaks, both of Okla.; Eric G. Montag, Van Nuys, Calif.

[73] Assignee: Royce Medical Company, Camarillo, Calif.

[21] Appl. No.: 17,818

[22] Filed: Feb. 16, 1993

[51] Int. Cl.⁵ .................. A43B 13/38; A61F 5/00; A61F 5/37
[52] U.S. Cl. ............................ 36/88; 36/93; 36/95; 36/110
[58] Field of Search ............... 36/43, 44, 71, 88, 95, 36/93, 110, 140, 155; 602/23

[56] References Cited

U.S. PATENT DOCUMENTS

| | | | |
|---|---|---|---|
| 975,576 | 11/1910 | Sexton | 36/140 |
| 2,909,854 | 10/1959 | Edelstein | 36/140 |
| 2,979,835 | 4/1961 | Scholl | 36/44 |
| 3,859,746 | 1/1975 | Kemp | 36/71 |
| 4,100,686 | 7/1978 | Sgarlato et al. | 36/44 |
| 4,571,853 | 2/1986 | Medrano | 36/44 |
| 4,793,078 | 12/1988 | Andrews | 36/44 |
| 4,869,001 | 9/1989 | Brown | 36/44 |
| 4,893,418 | 1/1990 | Ogden | 36/44 |
| 5,078,128 | 1/1992 | Grim et al. | 602/23 |
| 5,154,682 | 10/1992 | Kellerman | 36/44 |
| 5,197,942 | 3/1993 | Brady | 602/23 |

Primary Examiner—Paul T. Sewell
Assistant Examiner—Marie Denise Patterson
Attorney, Agent, or Firm—Poms, Smith, Lande & Rose

[57] ABSTRACT

Footgear is provided with an inner sole having a grid of removable resilient elements to permit removal of selected elements to provide relief to ulcerated or otherwise injured areas of the foot. An air bladder may underlie the inner sole, preferably with additional cushioning material within the air bladder. A walker with a soft goods type support may be provided with the foregoing type of inner sole within the support.

16 Claims, 4 Drawing Sheets

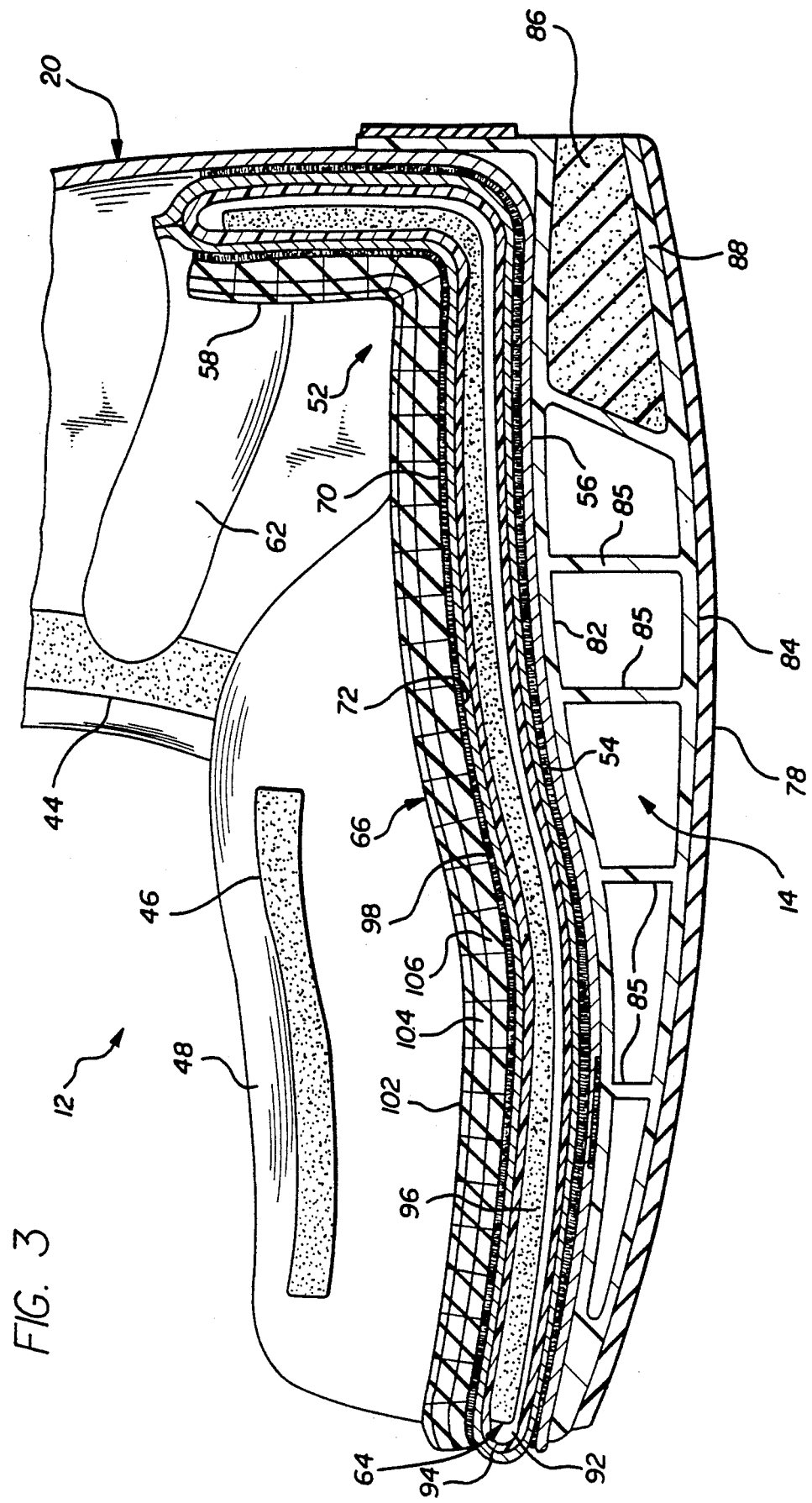

FOOTGEAR WITH PRESSURE RELIEF ZONES

RELATED PATENT APPLICATIONS

This invention is related to that disclosed in U.S. patent application Ser. No. 07/965,750, filed Oct. 23, 1992, entitled "Orthopaedic Support and Method for Providing Semi-Permanent Relief Zones," assigned to the assignee of this invention.

FIELD OF THE INVENTION

This invention relates to footgear having orthopaedic soles providing pressure relief areas for the feet.

BACKGROUND OF THE INVENTION

The problems solved by the present invention were discussed at length in the prior patent application cited above, and the background section of that application will therefore be repeated here.

Support pads are used in a wide variety of applications to provide cushioned support to an injured or otherwise sensitive bodily appendage. Such pads have the dual purpose of (1) providing orthopaedic support to the appendage and (2) protecting the appendage from further injury or damage resulting from contact with a foreign object or hard surface.

One common use of a support pad is as a cushioned foot sole in specialized footwear such as soft boots or patient walkers. These devices generally employ some type of soft, resilient material, such as foam, to provide cushioned support of a sensitive or damaged foot.

A particular problem arises when it becomes necessary to provide uneven support across the outer surface of an appendage. For example, an ulcerated appendage, often found in diabetic patients, requires pressure relief to the ulcerated area to allow healing. In this instance, it is desirable to have a pad which will apply cushioned support to the appendage, while refraining from supporting the afflicted area. For diabetic patients, the feet are commonly beset with such ulcerations, and it is therefore desirable to provide a cushioned support sole for a shoe or walker which is capable of providing specific zones of pressure relief.

Other approaches have addressed the problem of providing cushioned foot support. U.S. Pat. No. 2,598,217 (Bronson), issued May 27, 1952, discloses an invalid's boot with a thick insole. However, these approaches require replacement of the sole for each new patient, or for each new area of the original patient's foot which must be relieved.

U.S. Pat. No. 3,760,056 (Rudy), teaches a method for conforming a ski boot to the foot of the wearer by heating an inflatable bladder, distending it to the desired shape, and then cooling and deflating the bladder. The bladder can be subsequently be re-inflated to fit the wearer's foot. This method requires a mechanism for heating, which may be inconvenient or impractical when applied to a conformable sole. In the method disclosed, the inflatable bladder was placed over the foot to contact opposing sides, rather than underneath it as a support. Moreover, the elastomeric materials described in the Rudy patent typically may not provide the requisite comfort and cushioning generally required in a healing device.

A further method of providing support to an injured foot is disclosed in U.S. Pat. No. 5,078,128 (Grim, et al.) in which a removable leg walker includes a plurality of inflatable and adjustable bladder members in order to provide variable amounts of pressure to an affected limb as leg swelling increases or decreases. However, the bladder members of the Grim device do not retain their shape except as restrained by the surface of the appendage itself and thus do not provide the desired semi-permanent areas of relief to an injured appendage.

Incidentally, the above-cited U.S. patent application Ser. No. 07/965,750 discloses arrangements which provide relief using a pad of particulate material which is vacuum formed to the desired configuration.

From an overall standpoint, a principal object of the present invention is to provide a comfortable cushioned sole which may be conveniently modified to provide pressure relief to specific areas of the wearer's foot.

Another important object of the invention is to furnish a device which may be reused to provide relief to different areas of the patient's foot, or which may be used by other patients.

A further object is to provide a method for conforming a cushioned sole to the foot of a particular wearer, and of later reforming or returning the sole to its original shape.

SUMMARY OF THE INVENTION

In accordance with one illustrative embodiment of the invention, a walker frame, including an outer sole and side struts may be provided with an air bladder mounted above the outer sole, and a special inner sole mounted above the bladder and made up of a large number of separate resilient sections removably secured to a flexible sheet to form a substantially flat surface for engagement by the foot. In areas where the foot is ulcerated or otherwise injured, sections of the inner sole are removed to provide pressure relief.

In accordance with a broader aspect of the invention, footgear or footwear generally may be provided with an inner sole having mobile sections of the type described in the preceding paragraph.

With regard to the walker embodiment, a flexible soft goods-type support may be provided, to enclose the patient's foot, and having arrangements for securing to the walker frame. The bladder may be mounted between the outer sole and support, layered within the soft goods support, or preferably above the soft goods support. A dorsum strap may be secured to the support or the inner sole and extend around the ankle and instep, to hold the foot in place on the inner sole.

Additional features of the invention may include the following:

1. The removable sections may be held in place by pressure sensitive adhesive or preferably hook and loop type securing material of the Velcro type to permit removal and replacement of the sections.

2. The removable sections may be in a grid like configuration, using hexagonal, rectangular or square patterns.

3. The inner sole may have multiple layers, with the layer closest to the foot being softer and more resilient than other layers.

4. The inner sole may extend to the rear and upward to cushion the rear of the heel.

5. The bladder may be filled with fluid, air, other gas, liquid, or gel material.

6. The bladder may contain additional resilient material such as a layer of foam, for extra cushioning of the foot.

Other objects, features and advantages of the invention will become apparent from the following detailed description and from the accompanying drawings.

BRIEF DESCRIPTION OF THE DRAWINGS

FIG. 3 is a partial cross-sectional view taken along lines 3—3 of FIG. 1;

DETAILED DESCRIPTION OF PREFERRED EMBODIMENTS

Figure 1:
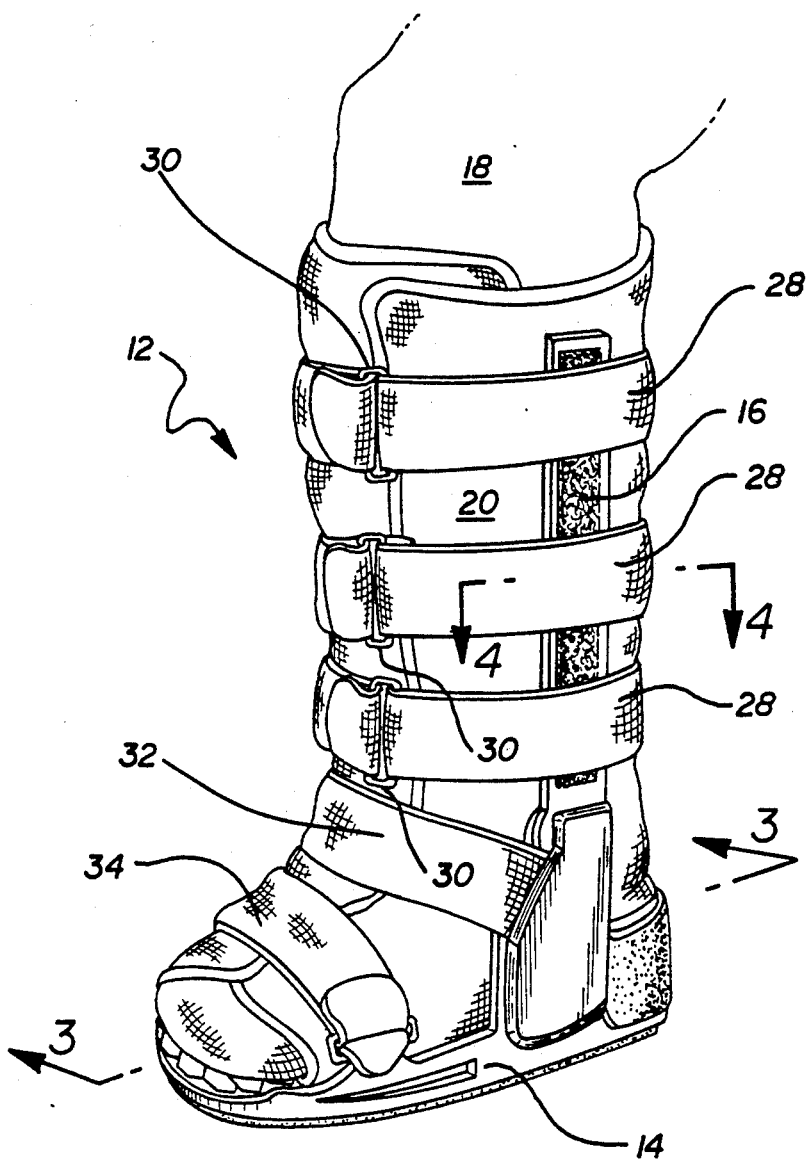
FIG. 1 is a perspective view of a walker of the type to which the present invention is applicable.
Figure 4:
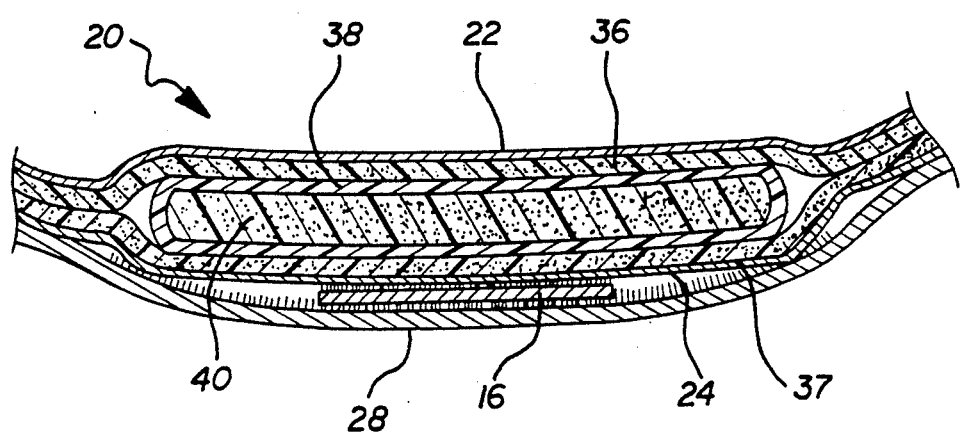
FIG. 4 is a cross-sectional view taken along lines 4—4 of FIG. 1.

Referring more particularly to the drawings, FIG. 1 shows a walker 12 including a frame made up of an outer sole assembly 14 and two side struts 16 secured to the sole, and extending up on either side of the lower leg of the patient 18. Within the frame 14, 16, is a soft goods type support member 20 for enclosing the lower leg, ankle and most of the foot of the patient or user. As best shown in FIG. 4, the soft goods type body member 20 includes outer cloth material 22 and 24 separated by two layers of foam 36 and 37, which may be either foam rubber or foamed urethane, by way of examples. The soft goods type body member 20 may be held in position within the frame 14, 16, by pads of hook and loop type material on the inner surface of the struts 16, and by the straps 28 extending around the struts 16, through the D-rings 30 and then being folded back on the other portions of the straps, and held in adjustable positions by mating Velcro type hoop and loop areas on the surfaces of the straps. The straps 32 and 34 across the instep and the forward portion of the assembly, operate in similar manners to hold the foot and the soft goods type support member 20 in position within the frame 14, 16.

Incidently, with regard to the detailed construction of the walker frame, reference is made to U.S. Pat. No. 5,078,128, granted Jan. 7, 1992, and assigned to the assignee of the present invention.

One of the straps 28 is also visible in FIG. 4 as is one of the struts 16. Between the body member 20 and the strut 16, and between the strut 16 and the strap 28, is hook and loop type material, so that various members are secured in place relative to one another.

Within the side walls of the soft goods body member 20, may be air bladders such as that shown at reference numeral 38 in FIG. 4 and preferably containing a layer of open cell foam 40. The bladder 38 may be located between one layer of foam 36 and fabric 22 and the second layer of foam 37 and fabric 24. This arrangement provides additional cushioning for the lower leg of the patient, particularly in the vicinity of the struts 16.

Figure 2:
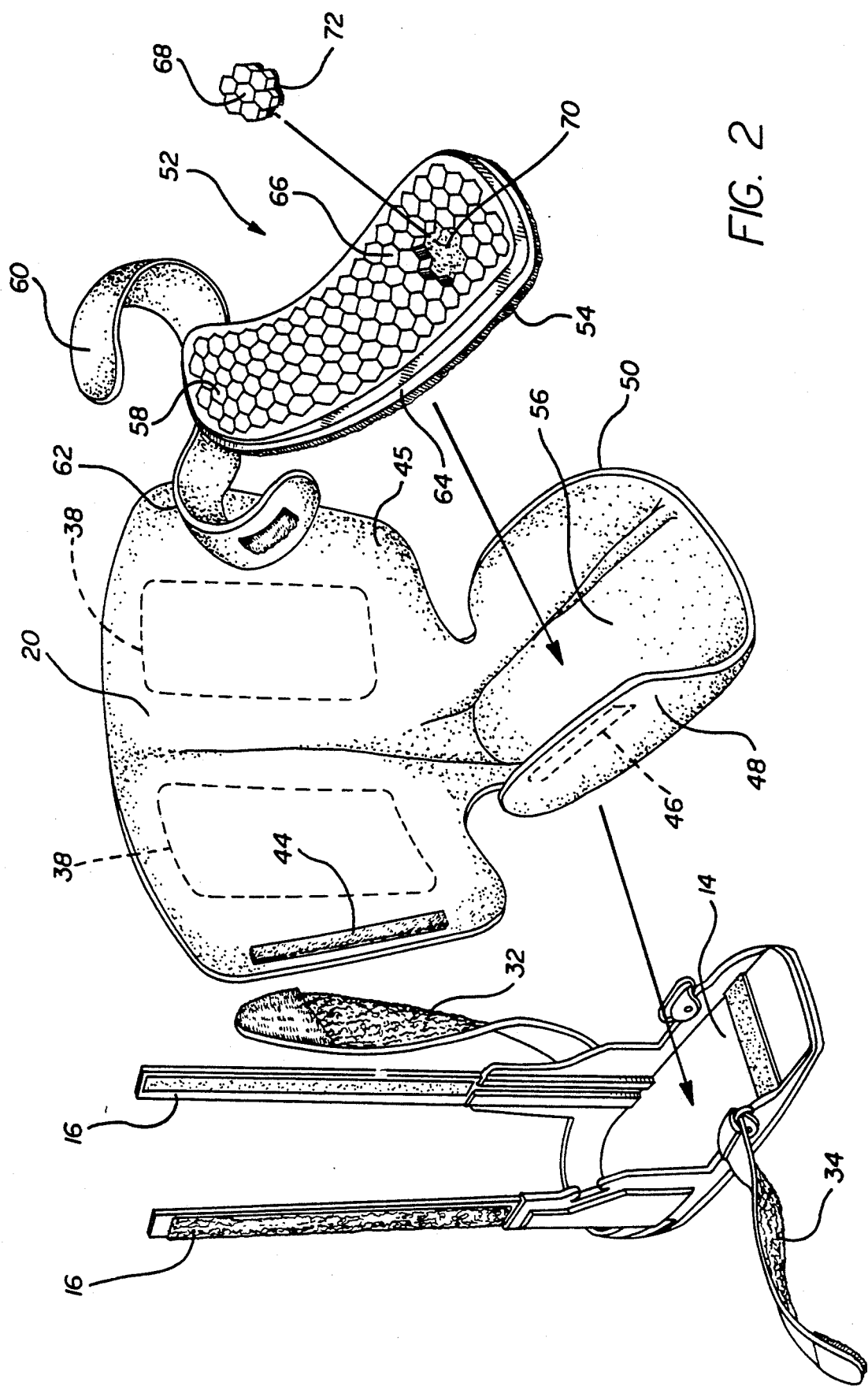
FIG. 2 is a partial exploded view of the walker of FIG. 1.

FIG. 2 is a partial exploded view of the walker of FIG. 1, with reference numerals employed in FIG. 1 being carried over to FIG. 2. Shown in FIG. 2 is the elongated pad 44 of hook type material. The outer cloth covering of the soft goods type body member 20 is of cloth of one of the well known types such as brushed nylor material which will receive hook type securing pads, such as that sold under the trademark "Velcro" so that the front upper portion of the soft goods type support member 20 may be held in the closed position by the engagement of the pad 44 with the outer surface of the mating portion 45 of the support member 20. Similarly, the pad 46 on the inner surface of the front flap 48 of the soft goods support member 20 serves to engage the mating flat 50 on its outer surface, and holds the front portion of the soft goods member around the upper portion of the patient's foot.

The footgear of the present invention is provided with an inner sole assembly 52 which is preferably mounted within the soft goods support member 20 by a layer of hook type securing material 54 which is on the lower surface of the assembly 52, and which engages the inner surface of the soft goods type support member 20 in the area 56 as shown in FIG. 2. The rear portion 58 of the inner sole assembly 56 may extend up behind the heel of the patient to cushion this area of the foot; and the straps 60 and 62, formed of soft material and held together by hook and loop type securing arrangements, served to hold the patient's foot back into proper engagement with the inner sole assembly 52.

Inner Sole assembly 52 includes a lower air bladder 64 which may contain a layer of foam material, and an upper resilient layer 66 constituting separate removable sections which together form a normally substantially smooth surface for engagement by the foot. These sections are individually removable, as indicated by the sections 68 which are shown removed from the space 70 where they would normally be located to complete the smooth upper surface of the inner sole assembly 52. The concept, as mentioned in the introductory portion of the present specification, is to provide relief to ulcerated or injured portions of the foot, whereby the foot is supported on the adjacent resilient material, with relief provided in the areas where the removable sections have been taken away. Note that the individual resilient sections such as the section 68, have hook or loop type securing material 72 on their lower surfaces, and the upper surface of the bladder 64 has mating hook and loop type material for removably securing sections such as section 68 in place to provide a relatively smooth upper surface. Thus, the group of sections 68 may be reinserted and re-secured into the opening 70, and other sections removed, to accommodate different needs, or the problems of another patient. Instead of using hook and loop type securing material as shown in FIG. 2, the lower surface of sections such as the sections 68 may be provided with pressure sensitive adhesive, thereby providing the removable and replaceable functions as discussed hereinabove.

FIG. 3 is a somewhat schematic cross-sectional view taken along line 3—3 of FIG. 1. More specifically, the view of FIG. 3 includes the soft goods type support member 20 which is here shown as a single layer for simplicity, but which, in reality, would be two layers of cloth and two foam layers forming a central foam core, as discussed in connection with FIG. 4. In addition, FIG. 3 shows the outer sole 14 including the lower tread portion 78, which would normally be somewhat rough for traction, the flap 48, the strap 62, the bladder 64, and the resilient inner sole 66.

Concerning the sole 14, in addition to the outer tread portion 78, it may include the upper and lower high strength plastic sheet members 82 and 84 which are interconnected by appropriate ribs 85. At the rear of the sole 14 is a cantilevered area in which resilient foam material 86 is located, so that controlled flexing of the rear heel end 88 of the lower plastic sheet member 84 provides increased cushioning for the patient, against shock to which he or she might otherwise be subjected.

Regarding the bladder assembly 64, it may include a sealed bladder made of thin sheet urethane 92 covered with cloth material 94, and containing an open cell foam layer 96 which may be bonded to the upper or lower surface of the bladder. Between the upper surface of the bladder assembly 64, and the lower surface of the inner sole 66 is a suitable material 98, for removably securing the inner sole 66 to the upper surface of the bladder 64. Material 98 may be hook and loop type material, or pressure sensitive adhesive, as noted hereinabove. The inner sole 66 may be formed of three layers 102, 104 and 106, which are bonded together. These three layers 102, 104 and 106 may be of progressively different softness and resiliency, with the softest and most resilient layer being the layer 102 closest to the foot, with layers 104 and 106 being progressively less resilient and providing somewhat greater support.

With regard to the construction of the outer sole assembly 14, it may be formed as described hereinabove in the cited U.S. Pat. No. 5,078,128, or may be of any other desired configuration. The present invention is primarily directed to a configuration of the inner sole, and the precise configuration of the outer sole arrangements may be chosen from many alternatives.

Figure 5:
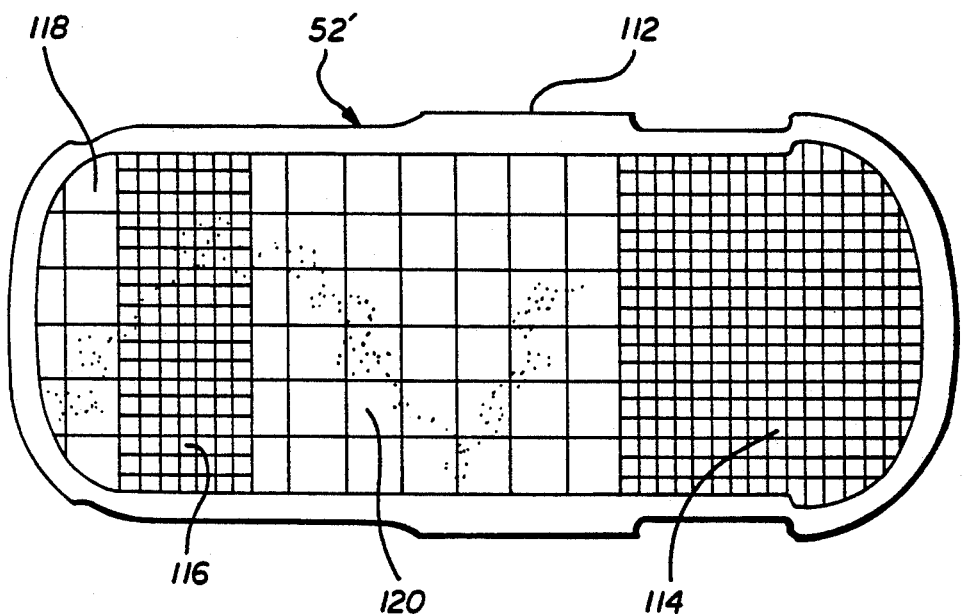
FIG. 5 is a top view of an alternative inner sole configuration.

FIG. 5 shows an alternative arrangement of the individual removable sections of the inner sole which is designated by the reference numeral 52'. In addition to the continuous outer rim 112, the sections are rectangular, or square, and have a closer spacing in the heel area 114, and in the area 116 immediately behind the toes. The area 118 where the toes would be located, and the central area 120 below the instep, could have larger sections, as these areas are less likely to have ulcerations and require relief. It is noted in passing, however, that the hexagonal configuration as shown in FIG. 2, is the presently preferred embodiment.

Figure 6:
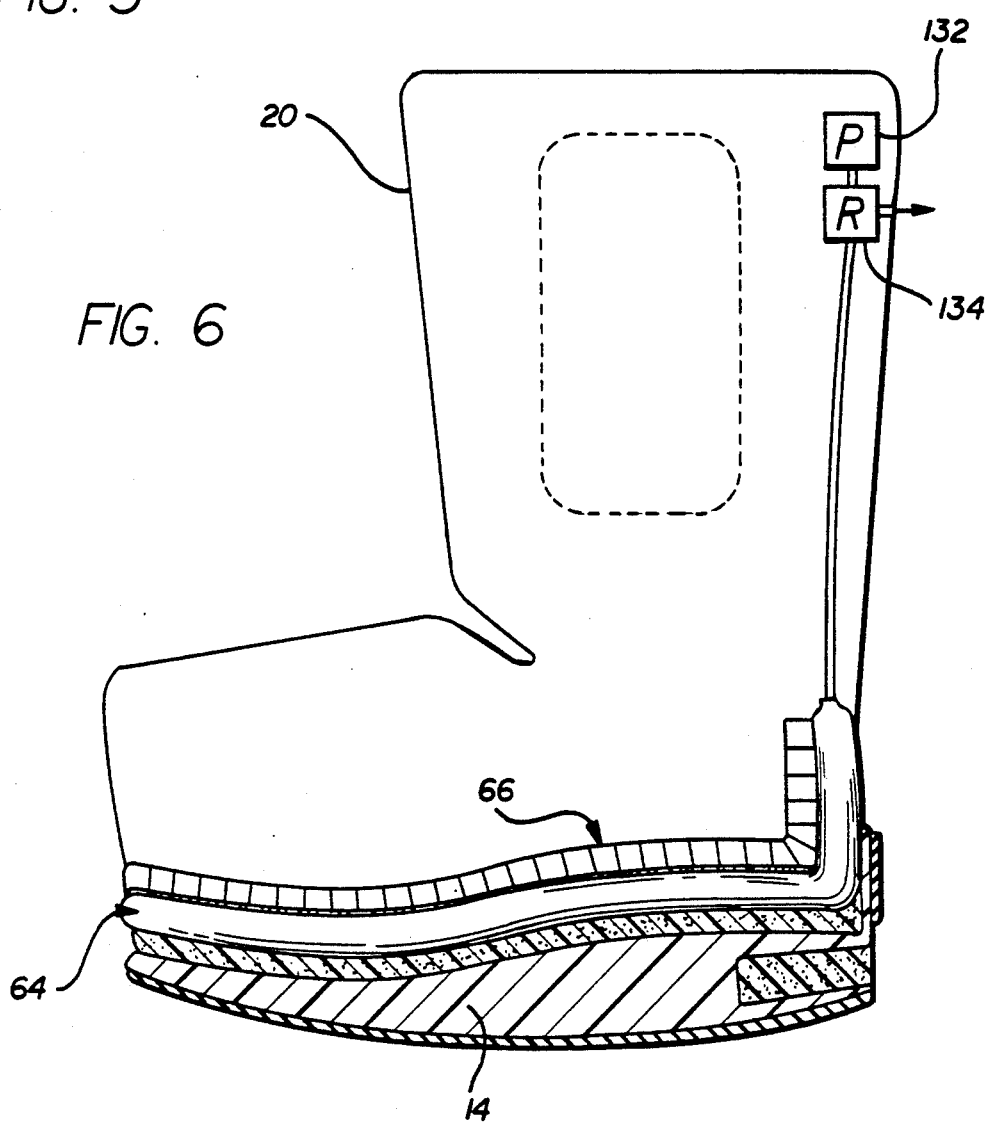
FIG. 6 is a schematic showing of a walker system implementing the principles of the invention.

Regarding FIG. 6, this is a schematic showing of a walker illustrating the principles of the invention and shows the soft goods type support 20, the sole 14, the bladder 64, and the inner sole 66. The bladder 64 may be a sealed bladder, preinflated, or may be provided with a pump 132, and pressure relief arrangements 134. The pump 132 may be manually actuated, mechanically actuated, or may be actuated by a walking or running action of the user. The pressure relief arrangements 134 may involve a simple adjustable spring and ball type controlled pressure relief valve, or may involve more complex pressure sensing and valve actuation arrangements controlled by the sensing of the pressure.

Concerning the dimensions of the removable sections, one operative and presently preferred embodiment of the invention employs hexagonal removable elements of the type shown in FIG. 2, with the hexagons having a distance between opposing faces of approximately ⅜". Larger or smaller removable sections could be employed; however, it is preferred that the sections have a linear extent less than ⅞".

In conclusion, a number of illustrative embodiments of the invention been discussed hereinabove. However, it is to be understood that various changes and modifications may be made without departing from the spirit and scope of the invention. Thus, by way of example and not of limitation, the air bladder under the sole may be embedded in the soft goods member or may be located under it, between the soft goods support member 20 and the outer sole assembly 14. In addition, the inner sole 66 may be employed without the underlying bladder, although the use of the underlying bladder is preferred. The invention is, of course, applicable to other types of footgear, in addition to walkers, for example, athletic shoes or normal walking shoes. Accordingly, the present invention is not limited to the precise embodiments described hereinabove.

What is claimed is:

1. A walker including pressure relief areas for the foot comprising:
   a walker frame including an outer sole and struts extending from said sole upward;
   a soft goods type support for enclosing the ankle, lower leg and at least a substantial portion of the foot;
   means for securing said support to said frame;
   a bladder for containing air mounted in said walker above said outer sole;
   an inner sole mounted in said walker above said bladder, said inner sole having a plurality of relief zone areas arranged in a grid pattern constituting separate resilient sections removably secured on their lower surfaces to an underlying flexible sheet and together forming a normally substantially smooth surface for engagement by the foot, said sections being individually removable to provide localized pressure relief to selected areas of the foot; and
   said resilient sections being directly adjacent one another to form said grid;
   whereby one or a plurality of said adjacent sections may be removed at any desired area of the inner sole to provide relief corresponding to the afflicted zone of the foot.

2. A walker as defined in claim 1 wherein said inner sole has a grid configuration with said removable sections being hexagonal.

3. A walker as defined in claim 1 wherein said inner sole has a grid configuration with said removable sections are rectangular.

4. A walker as defined in claim 1 wherein said inner sole includes a plurality of layers, with the layer closest to the foot being substantially softer and more resilient than other layers.

5. A walker as defined in claim 1 wherein said inner sole extends to the rear beyond the heel of a patient and upward along the rear surface of the heel.

6. A walker as defined in claim 1 further comprising means connected to said support for extending around the instep to hold the foot back into said support and in engagement with said inner sole.

7. A walker as defined in claim 1 whereon hook and loop type fabric fastening arrangements are provided to hold the support to the walker frame, and onto the patient's foot.

8. A walker as defined in claim 1 further comprising resilient material within the bladder for providing additional cushioning for the foot.

9. Footgear including pressure relief areas for the foot, comprising:
   an outer sole;
   a bladder for containing fluid, mounted in said footgear above said outer sole;
   said footgear including a plurality of relief zone areas arranged in a grid pattern constituting separate resilient sections removably secured on their lower surfaces and together forming a normally substantially smooth surface for engagement by the foot, said sections being individually removable to provide localized relief to selected areas of the foot;

said separate resilient sections being mounted in said footgear above said bladder;

said resilient sections being directly adjacent one another to form said grid; and each said resilient section having a thickness or depth comparable to its maximum transverse dimension;

whereby one or a plurality of said adjacent sections may be removed at any desired area of the inner sole to provide relief corresponding to the afflicted zone of the foot.

10. Footgear including pressure relief areas for the foot, comprising:

an outer sole;

a bladder for containing fluid, mounted in said footgear above, said outer sole; and an inner sole mounted in said footgear above said bladder, said inner sole having a plurality of relief zone areas arranged in a grid pattern constituting separate resilient sections removably secured on their lower surfaces to an underlying flexible sheet and together forming a normally substantially smooth surface for engagement by the foot, said sections being individually removable to provide localized relief to selected areas of the foot;

said resilient sections being directly adjacent one another to form said grid; and said grid comprising most of said inner sole.

11. Footgear as defined in claim 10 wherein said inner sole has a grid configuration with said removable sections being hexagonal.

12. Footgear as defined in claim 10 wherein said inner sole has a grid configuration with said removable sections being rectangular.

13. Footgear as defined in claim 10 wherein said inner sole includes a plurality of layers, with the layer closest to the foot being substantially softer and more resilient than other layers.

14. Footgear as defined in claim 10 wherein said inner sole extends to the rear beyond the heel of the patient and upward along the rear surface of the heel.

15. Footgear as defined in claim 10 further comprising means forming part of said footgear for extending around the instep to hold the foot back into engagement with said inner sole.

16. Footgear including pressure relief areas for the foot, comprising:

an outer sole;

a bladder for containing fluid, mounted in said footgear above, said outer sole; and an inner sole mounted in said footgear above said bladder, said inner sole having a plurality of relief zone areas arranged in a grid pattern constituting separate resilient sections forming a normally substantially smooth surface for engagement by the foot, said sections being individually removable to provide localized relief to selected areas of the foot;

said grid comprising most of said inner sole;

said resilient sections being directly adjacent one another to form said grid; and each said resilient section having a thickness or depth comparable to its maximum transverse dimension;

whereby one or a plurality of said adjacent sections may be removed at any desired area of the inner sole to provide relief corresponding to the afflicted zone of the foot.

* * * * *